US00PP11610P

United States Patent [19]

Olesen et al.

[11] Patent Number: Plant 11,610

[45] Date of Patent: Oct. 31, 2000

[54] COMPACT FLORIBUNDA ROSE PLANT NAMED 'POULGRAD'

[75] Inventors: L. Pernille Olesen; Mogens N. Olesen, both of Fredensborg, Denmark

[73] Assignee: Poulsen Roser ApS, Fredensborg, Denmark

[21] Appl. No.: 09/177,976

[22] Filed: Oct. 22, 1998

[51] Int. Cl.[7] ..... A01H 5/00

[52] U.S. Cl. ..... Plt./151

[58] Field of Search ..... Plt./150, 151, 129, Plt./122

*Primary Examiner*—Howard J. Locker

[57] ABSTRACT

A new compact floribunda rose plant which has abundant, non-fading, red flowers and attractive foliage. The variety successfully propagates from softwood cuttings and by traditional budding, and is adapted to production in containers in commercial glasshouses and nurseries. This new and distinct variety has shown to be uniform and stable in the resulting generations from asexual propagation.

1 Drawing Sheet

SUMMARY OF THE INVENTION

The present invention constitutes a new and distinct variety of compact floribunda rose plant which originated from a controlled crossing between an unnamed seedling and 'POULmax', U.S. Plant patent application Ser. No. 09/277,238. The two parents were crossed and the resulting seeds were planted in a controlled environment. The new variety is named 'POULgrad'.

The new rose may be distinguished from its seed parent, an unnamed seedling created by the same inventors, by the following combination of characteristics:

1. The unnamed seedling grows taller in height than 'POULgrad'.
2. The flowers of the unnamed seedling are more double and darker in color than the flowers of 'POULgrad'.

The new variety may be distinguished from its pollen parent, 'POULmax' created by the same inventors, by the following combination of characteristics:

1. The flower color of 'POULmax' is salmon-orange and the flower color of 'POULgrad' is dark red.
2. 'POULmax' U.S. Plant patent application Ser. No. 09/277,238 has taller and more bushy growth than 'POULgrad'.

The objective of the hybridization of this rose variety for commercial greenhouse and nursery culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULgrad' from all other varieties of which we are aware.

As part of their rose development progam, L. Pernille Olesen and Mogens N. Olesen germinated the seeds from the aforementioned hybridization and conducted evaluations on the resulting seedlings in a controlled environment in Fredensborg, Denmark.

'POULgrad' was selected by the inventors as a single plant from the progeny of the hybridization in April, 1992.

Asexual reproduction of 'POULgrad' by cuttings was first done in their nursery in Fredensborg, Denmark in May, 1993 and by traditional budding in their nursery in Fredensborg, Denmark in August, 1993 by L. Pernille and Mogens N. Olesen. This initial and other subsequent propagations conducted in controlled environments have demonstrated that the characteristics of 'POULgrad' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULgrad'. Specifically illustrated in SHEET 1:

1. Apical portion of a flowering branch showing bud, flower, and leaf attachment;
2. Flower bud, partially opened bud, and open bloom;
3. Flower petals, detached;
4. Sepals, receptacle, and pedicel;
5. Flowering stem exhibiting thorns;
6. Leaves.

DETAILED DESCRIPTION OF THE VARIETY

The following is a description of 'POULgrad', as observed in its growth in glasshouses in Fredensborg, Denmark; and in a field nursery in Jackson County, Oreg. Color references are made using The Royal Horticultural Society (London, England) Colour Chart, 1995, except where common terms of color are used.

For a comparison, several physical characteristics of the rose variety 'POULskov', a patented rose variety from the same inventors described and illustrated in U.S. Plant Pat. No. 9,062 and issued on Feb. 28, 1995 are compared to 'POULgrad' in Chart 1.

CHART 1

| | 'POULgrad' | 'POULskov' |
|---|---|---|
| Flower bud color, ¼ open | Red Group 46A | Between Red Group 55D and 56A |
| Petal count | 25–30 petals | 50–60 petals, and numerous petaloids. |

Parents: Unnamed seedling×'POULmax', U.S. Plant patent application Ser. No. 09/277,238.

Classification:
*Botanical.*—*Rosa hybrida.*
*Commercial.*—Compact floribunda.

FLOWER AND FLOWER BUD

Blooming habit: Continuous.
Flower bud:
*Size.*—Upon opening, 24 mm–26 mm in length from base of receptacle to end of bud.
*Bud form.*—Pointed ovoid.
*Bud color.*—As sepals unfold, Red Group 53A. Red Group 46A at ¼ opening.
*Sepals.*—Green Group 138A–B. Weak foliaceous appendages on three of the five sepals. Surfaces of other sepals slightly pubescent. Stipitate glands present on some margins.
*Receptacle.*—Surface: Smooth. Glabrous. Shape: Urn-shaped. Size: Medium-large. 8 mm (h)×7 mm (w). Color: Green Group 138B.
*Peduncle.*—Surface: Smooth, glabrous. Length: 40–60 mm range of length. Color: Green Group 138A–B. On plants grown under high light conditions, pedunculs may exhibit intonations of Greyed-Red Group 180A. Strength: Upright.
*Borne.*—Singly and in small clusters.
Flower bloom:
*Fragrance.*—Light floral scent.
*Duration.*—As a pot plant, flowers last from 8 to 12 days. As a cut flower 6 to 8 days. Petals fall cleanly away from plant.
*Size.*—Medium for a 15 cm pot rose. Average flower diameter is 55 mm when open.
*Form.*—Flower exhibits floral parts when open.
*Shape of flower when viewed from the side.*—Upon opening, upper part: Flattened convex. Upon opening, lower part: Flattened convex. Open flower, upper part: Flat. Open flower, lower part: Flat to Flattened convex.
*Petalage.*—Double. Average range: 25–30 under normal conditions with no petaloids.
Color:
*Upon opening, petals.*—Upper Surface: Red Group 53A. With lustrous, velvet-like sheen. Reverse Side: Red Group 53B.
*Upon opening, basal petal spots.*—Outer Side: Yellow Group 4B. Inner Side: Yellow Group 4B.
*After opening, petals.*—Upper Surface: Red Group 53A. With lustrous, velvet-like sheen. Reverse Side: Red Group 53C.
*After opening, basal petal spots.*—Outer Side: Yellow Group 4C. Inner Side: Yellow Group 4C.
General tonality: On open flower Red Group 53A-46A. No change in the general tonality at the end of the 3–4th day. Afterwards, general tonality is Red Group 46A.
Petals:
*Petal reflex.*—Petals nearly flat. Petals reflex only slightly.
*Petal edge.*—Uniform.
*Shape.*—Round.
*Petaloids.*—Commonly none.
*Thickness.*—Thick.
*Arrangement.*—Informal.
Reproductive organs: Visible on open blooms.
*Pollen.*—Color: Yellow Group 13B. Abundance: Average.
*Anthers.*—Size: Small to medium.
*Color.*—Orange Group 24A-26A. Abundance: Above average.
*Filaments.*—Color: Upper filament is Orange-Red Group 34A. Lower portion of filament is Yellow-Green Group 154C.
*Stigmas.*—Positioned 2–3 mm above anthers. Color: Greyed-Green Group 193C.
*Styles.*—Color: Greyed-Green Group 193C. Other intonations: Light intonations of Red-Purple Group 66C on upper ¼ of style.
*Hips.*—None observed.

PLANT

Plant growth: Moderate grower. Compact and upright. When grown as a 15 cm pot plant, the average height of the plant itself is 22 to 24 cm and the average width is 20 to 22 cm. When grown as a budded field grown plant, the average height of the plant itself is 50–60 cm and the average width is 45–55 cm.
Stems:
*Color.*—Young wood: Green Group 138B. Older wood: Green Group 138B.
*Prickles.*—Incidence: With 10–12 thorns per 10 cm of stem. Size: Average length: 8 mm–9 mm. Color: Thorns change to mature color quickly. Young: Yellow-Green Group 145C. Mature: Greyed-Orange Group 164C. Shape: Linear.
*Surface.*—Young wood: Smooth. Older wood: Smooth.
Plant foliage: Normal number of leaflets on normal leaves in middle of the stem: 5–7 leaflets. If 7 leaflets, lowermost 2 leaflets reduced in size.
*Leaf size.*—Small-medium. 75–85 mm (l)×50–55 mm (w).
*Abundance.*—Below average abundance.
*Color.*—Upper Leaf Surface: Green Group 137A. Lower Leaf Surface: Green Group 138B. Juvenile foliage: Green Group 143B–C. On plants grown under high light conditions, underside and upper and lower leaf margins may exhibit intonations of Greyed-Red Group 180A. Anthocyanin intonation: Generally very weak, however on plants grown under high light conditions, underside and upper and lower leaf margins may exhibit intonations of Greyed-Red Group 180A.
Plant leaves and leaflets:
*Stipules.*—Present. Stipitate glands present on margins. Size: 9 mm–10 mm. Color: Green Group 137D. Presence of stipitate glands: On margins of stipules.
*Petiole.*—Length: 15 mm–30 mm. Color: Green Group 137D. On plants grown under high light conditions, petioles on juvenile foliage may exhibit intonations of Greyed-Red Group 180A. Underneath: Smooth. Margins: With limited number of stipitate glands.
*Rachis.*—Color: Green Group 137C. On plants grown under high light conditions, rachis on juvenile foliage may exhibit intonations of Greyed-Red Group 180A. Underneath: With moderate number of hairs and small prickles. Margins: With limited number of stipitate glands.
*Leaflet.*—Edge: Serrated. Shape: Ovate to rounded. Other: Margin of leaflet and leaflet petiolule with a limited number of stipitate glands present.
Disease resistance: Above average resistance to mildew, rust, black spot, and Botrytis under normal growing conditions in Jackson County, Oreg.

We claim:

1. A new and distinct variety of rose plant of the compact floribunda class, substantially as herein illustrated and described as a distinct and novel rose variety due to its abundant, red flowers, vigorous and compact growth, year round flowering under glasshouse conditions, suitability for production from softwood cuttings, and durable flowers and foliage which make the variety suitable for distribution in the floral industry.

* * * * *

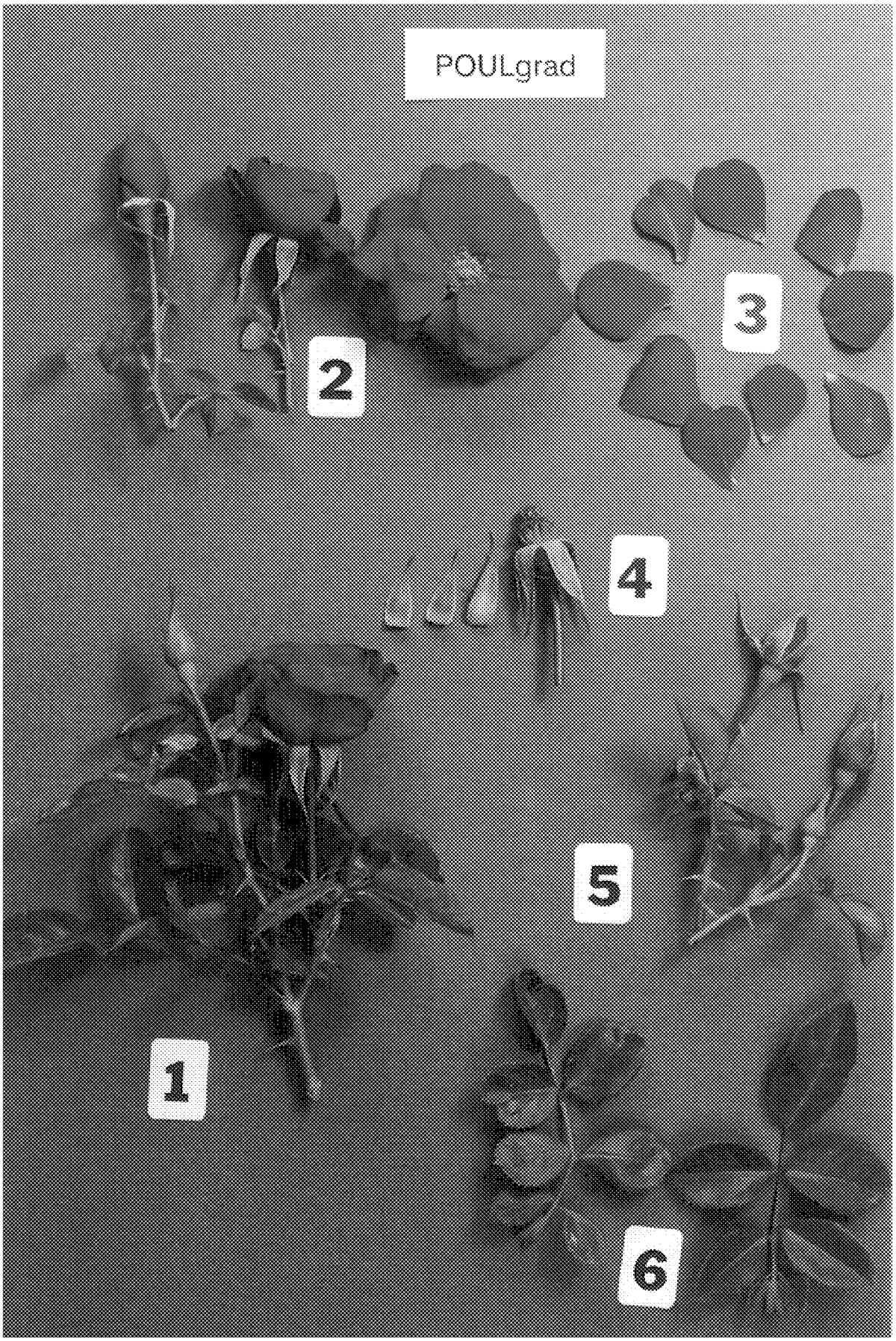
POULgrad
1
2
3
4
5
6